US011253483B2

(12) United States Patent
Tang et al.

(10) Patent No.: US 11,253,483 B2
(45) **Date of Patent: *Feb. 22, 2022**

(54) PROTEASE ASSISTED NATIVE-PROTEIN DELIVERY APPROACH (PANDA)

(71) Applicant: The Regents of the University of California, Oakland, CA (US)

(72) Inventors: Yi Tang, San Gabriel, CA (US); Zhen Gu, Los Angeles, CA (US); Yunfeng Lu, Culver City, CA (US); Ming Yan, Los Angeles, CA (US); Anuradha Biswas, Los Angeles, CA (US); Guoping Fan, Agoura Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 346 days.

This patent is subject to a terminal disclaimer.

(21) Appl. No.: 16/551,535

(22) Filed: Aug. 26, 2019

(65) Prior Publication Data

US 2020/0009070 A1 Jan. 9, 2020

Related U.S. Application Data

(60) Division of application No. 15/054,470, filed on Feb. 26, 2016, now Pat. No. 10,434,069, which is a continuation of application No. 13/089,117, filed on Apr. 18, 2011, now Pat. No. 9,283,194.

(60) Provisional application No. 61/324,887, filed on Apr. 16, 2010.

(51) Int. Cl.

| | |
|---|---|
| ***A61K 9/51*** | (2006.01) |
| ***A61K 31/7088*** | (2006.01) |
| ***A61K 41/00*** | (2020.01) |
| ***A61K 47/58*** | (2017.01) |
| ***A61K 38/02*** | (2006.01) |
| ***A61K 48/00*** | (2006.01) |

(52) U.S. Cl.

CPC .......... *A61K 9/5169* (2013.01); *A61K 9/5138* (2013.01); *A61K 9/5192* (2013.01); *A61K 31/7088* (2013.01); *A61K 38/02* (2013.01); *A61K 41/0042* (2013.01); *A61K 47/58* (2017.08); *A61K 48/00* (2013.01)

(58) Field of Classification Search

None

See application file for complete search history.

(56) References Cited

U.S. PATENT DOCUMENTS

| | | | |
|---|---|---|---|
| 6,716,450 | B1 | 4/2004 | Yin et al. |
| 7,056,901 | B2 | 6/2006 | Frechet et al. |
| 7,217,410 | B2 | 5/2007 | Suslick et al. |
| 2005/0008572 | A1 | 1/2005 | Prokop et al. |
| 2008/0248126 | A1 | 10/2008 | Cheng et al. |
| 2008/0312134 | A1 | 12/2008 | Hirt et al. |
| 2010/0010102 | A1 | 1/2010 | Roy et al. |

OTHER PUBLICATIONS

Biswas, A. et al., "Endoprotease-Mediated Intracellular Protein Delivery Using Nanocapsules," ACS Nano, 5 (1385) 2011.
Gu, Z. et al., "Tailoring Nanocarriers for Intracellular Protein Delivery," Chemical Society Reviews, in press, 2011.
Gu, Z. et al., "Detection of Mercury Ion by Infrared Fluorescent Protein and Its Hydrogel-Based Paper Assay," Analytical Chemistry, 83(2324), 2011.
Gu, Z. et al., "Probing Protease Activity by Single-Fluorescent-Proteing Nanocapsules," Chemical Communications, 46 (6467), 2010.
Gu, Z. et al., "Enzyme-Assisted Photolithography for Spatial Functionalization of Hydrogels," Lab on a Chip, 10 (1946), 2010.
Gu, Z. et al., "Hybrid Nanocomposites of Semiconductor Nanoparticles and Conjugated Polyelectrolytes and Their Application as Fluorescence Biosensors," Polymer, 51 (902), 2010.
Gu, Z. et al., "Protein Nanocapsule Weaved with Enyzmatically Degradable Polymeric Network," Nano Letters, 12 (4533), 2009.
Gu, Z. et al., "Biomolecular Nanopatterning by Magnetic Electric Lithography," Angewandte Chemie International Edition, 48(952), 2009.
Gu, Z. et al., "Dual Electroluminescence from a Single-Component Light-emitting Electrochemical Cell Based on Water-Soluble Conjugated Polymer," Journal of Applied Polymer Science, 100 (2930), 2006.
Joo, K-II et al., "Enhanced Real-Time Monitoring of Adeno-Associated Virus Trafficking by Virus-Quantum Dot Conjugates," ACS Nano, in press, 2011.
Lai, Q. et al., An Organic/Si Nanowire Hybrid Field Configurable Transistor, Nano Letters, 3 (876), 2008.
Sun, B. et al., "Conjugated Polymer Fluorescence Probe for Intracellular Imaging of Magnetic Nanoparticles," Macromolecules, 43 (10348), 2010.
PCT International Search Report and Written Opinion dated Sep. 30, 2010 (PCT International Application No. PCT/US2010/026678).
Zhao, M. et al., "Redox-Responsive Nanocapsules for Intracellular Protein Delivery," Biomaterials, in press, 2011.

(Continued)

*Primary Examiner* — Robert J Yamasaki
(74) *Attorney, Agent, or Firm* — Gates & Cooper LLP

(57) ABSTRACT

A method for intracellular delivery of single proteins or other cargo molecules by encapsulation within nanocapsules formed by interfacial polymerization of one or more types of monomers and selected protease cleavable cross-linkers is provided. The thin positively charged capsules are readily brought into the cytosol of target cells by endocytosis. The capsules are degraded by the action of endogenous proteases or co-delivered proteases on the cross-linkers releasing the functional cargo unaltered. The cross-linkers can be adapted to be cleavable by specific enzymes selected from available intracellular enzymes within the target cell or co-delivered or self-cleaving when the cargo itself is a protease. The nanocapsules produced by the methods have been shown to have long-term stability, high cell penetration capability, low toxicity and efficient protease-modulated specific degradability without affecting cargo protein function.

19 Claims, 9 Drawing Sheets

(56) References Cited

OTHER PUBLICATIONS

Singapore Written Opinion dated Jan. 17, 2013, Singapore Appln. No. 201106455-7.
Ge, J., et al., Molecular Fundamentals of Enzyme Nanogels, J Phys. Chem. B 2008, 112, pp. 14319-14324.
Yan, M., et al., A novel intracellular protein delivery platform based on single-protein nanocapsules, Nature Nanotechnology, 5, 48-53 (Nov. 22, 2009).
Yan, M., et al., Encapsulation of Single Enzyme in Nanogel with Enhanced Biocatalytic Activity and Stability, J. Am. Chem Soc. 2006, 128, pp. 11008-11009.
Yan, M., et al., Fabrication of Single Carbonic Anhydrase Nanogel against Denaturation and Aggregation at High Temperature, Biomacromolecules 2007, 8, pp. 560-565.
Calvo et al., Development of positively charged colloidal drug carriers: chitosan-coated polyester nanocapsules and submicron-emulsions, Colloid and Polymer Science, 1997, vol. 275, pp. 46-53.
Drury et al., Biomaterials, 2003, vol. 24, pp. 4337-4351.
Sukhorukov et al., Trends in Biotechnology, 2007, vol. 25, pp. 93-98.

(M1)

(M2)

(CL1)

(CL2)

(CL3)

PROTEASE ASSISTED NATIVE-PROTEIN DELIVERY APPROACH (PANDA)

CROSS-REFERENCE TO RELATED APPLICATIONS

This application is a divisional application that claims the benefit under 35 U.S.C. § 120 of U.S. patent application Ser. No. 15/054,470, filed Feb. 16, 2016, which is a continuation application that claims the benefit under 35 U.S.C. § 120 of U.S. patent application Ser. No. 13/089,117, filed Apr. 18, 2011, which claims priority under Section 119(e) from U.S. Provisional Application Ser. No. 61/324,887, filed on Apr. 16, 2010, the contents of each of which are incorporated herein by reference in their entirety.

STATEMENT REGARDING FEDERALLY SPONSORED RESEARCH OR DEVELOPMENT

This invention was made with government support under Grant Number HDTRA1-09-1-0001 awarded by the U.S. Department of Defense, Defense Threat Reduction Agency. The government has certain rights in the invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to drug delivery schemes and methods for producing biologically stable protein based nanostructures, and more particularly to compositions and methods for intracellular therapeutic protein delivery based on the formation of a protein nanocapsule having a single-protein core and a thin polymeric shell cross-linked by designed peptides that can be specifically recognized and cleaved by a protease to release the protein core.

2. Description of Related Art

Intracellular delivery of exogenous proteins holds great promise in biological and medical applications in humans and animals. For example, recombinant protein therapeutics is an attractive alternative to gene or siRNA transfections and may be useful in biological and medical applications, including cell cycle regulation, cellular immunity, transcription regulation and cancer treatments.

Protein therapeutics has enormous potential for the treatment of human diseases, especially those caused by the temporary or permanent loss of a type of functional protein. For example, many cancer cells do not undergo programmed cell death because proteins in the apoptosis machinery are either defective in function or attenuated in expression. Direct delivery of active proteins to the cytosol of cells could therefore restore or replenish the functions of interest and lead to the desired cell phenotypes. Additionally, introduction of recombinant proteins that can regulate transcription can exert artificial control of gene expression levels and could lead to the reprogramming of cell fate. In comparison to gene therapy, which is currently the predominant choice of delivery for promising protein therapeutics, direct protein delivery can bypass the requirement of permanent or unintended changes to the genetic makeup of the cell, and is therefore a safer therapeutic alternative.

Although protein-based drugs have had great commercial success, they still suffer from significant obstacles with in vivo efficacy, especially in the area of intracellular protein delivery. The development of intracellular protein therapeutics has been hampered by the limitations arising from the nature of proteins. These limitations include structural fragility, low serum stability and poor membrane permeability for most proteins that are negatively charged at pH 7. The poor stability and membrane impermeability of most native proteins make efficient delivery to the interior of cells difficult. For such technology to be successful, the exogenous protein needs to effectively penetrate the plasma membrane and to be efficiently released in the cytosol. Meanwhile, the biological activity of proteins should be resistant to denaturation and enzymatic degradation.

Different strategies that aim to protect protein integrity and activity as well as to aid with intracellular delivery have been explored. In spite of these efforts, no single technique has been widely applied because of the practical limitations of these approaches.

Among the various protein delivery approaches that have been pursued, are physical methods, such as electroporation and microinjection, a protein transduction domain (PTD)-mediated platform, and noncovalent methods based on a cationic carrier, such as liposomes or polymer particles.

However, each of these approaches has limitations that limit their usefulness. For example, physical methods such as microinjection can damage the target cells and the types of available in vivo purposes for the methods are limited.

Similarly, PTD based delivery systems that require a covalent attachment to the protein being delivered, either by creating a designed DNA construct or by a specific chemical conjugation, can impair the stability and activity of proteins in certain cases. Covalent approaches include genetic fusion of protein transduction domains and conjugation of polymers to free amine groups on the surface of proteins. However, these approaches often suffer from an alteration of protein activity due to modification of the protein structure.

Noncovalent based polymer carriers that encapsulate protein cargo via electrostatic assembly or hydrophilic and hydrophobic interactions have also been explored. These methods employ various materials to effectively help the protein travel into cells, albeit often suffer from instability in serum. However, it is still challenging to enhance delivery efficiency as well as to avoid the colloidal instability of the complex.

Accordingly, intracellular delivery of functional proteins has significant therapeutic implications in biological applications, including disease therapies, vaccination, and imaging. There is a need for a method for intracellular protein delivery and for a method for reliably producing a construct that is stable in serum and can readily enter the cytosol of target cells by endocytosis.

There is a particular need for an intracellular delivery system that can protect the protein cargo from denaturation and proteolysis during circulation and endocytosis; that can shield a negatively charged protein and provide an overall positive surface charge to facilitate internalization across the phospholipid membrane; and that can release the protein cargo in native form when the desired destination (i.e. the cytosol) is reached. The present invention satisfies these needs as well as others and is generally an improvement over the art.

BRIEF SUMMARY OF THE INVENTION

The present invention provides a novel platform for the delivery of native proteins and other molecules into living cells that is readily adaptable to a wide variety of biological systems and medical therapies. The methods should be adaptable to virtually any setting that would benefit from the delivery of selected cargo molecules to the interior of a cell. Many different types of molecules such as cytokines, transcription factors, enzymes, nuclear and other proteins along with other therapeutic agents, including small molecular anticancer drugs, small interfering RNA (siRNA), peptides and plasmid DNA and the like are suitable cargo molecules.

The intracellular delivery platform of the invention is centered on the production and delivery of selected cargo to target cells that is contained in stable, enzymatically degradable nanocapsules. The preferred nanocapsule consists of a single-protein core and a thin polymeric shell cross-linked by designed peptides, which can be specifically recognized and cleaved by a selected protease.

The cleavable cross-linkers will preferably include a peptide sequence or structure that is a substrate of a protease or other enzyme that has been selected. The peptide sequences that are incorporated in the structure of the cross-linkers can be varied and can be designed to be degraded by different proteases that will be present in the cytosol. The selection of protease and the associated substrate for incorporation in cross-linkers may follow three different strategies. The first and most common would be to select a peptide substrate of an endogenous protease widely existing inside mammalian cells, such as furin or that is specific to a target cell such as matrix metalloproteinases which are overexpressed in various human cancer cell lines, for example.

The second approach is to select a cargo protein which itself is a protease (such as caspase) that would be encapsulated with nanocapsules cross-linked by the peptide with the sequence that can be cleaved by the cargo protease itself. The resulting capsules are therefore self-degrading.

The third approach is to co-deliver a target protein together with an exogenous protease that has been encapsulated within nanocapsules cross-linked by the peptide substrate of the co-delivered protease.

In a preferred embodiment, single encapsulated proteins are prepared by first modifying the protein surface with vinyl groups, followed by polymerization using enzymatically cleavable peptide cross-linkers. In this embodiment, enzymatically degradable polymeric nanocapsules are produced in a two step, one-pot procedure. In the first step, monomers and prepared cross-linkers are deposited on the protein surface by physical adsorption, such as with electrostatic forces or van der Waals forces. This seeds the protein surface with sites for polymerization. Next, in situ free-radical polymerization is performed to form the protective shell in aqueous solution, facilitated by the bisacrolylated short peptide cross-linkers that can be specifically cleaved by selected proteases.

The resulting single cargo nanocapsules are of a uniform size and are typically smaller than 20 nm. The capsules produced by these methods have been shown to be water soluble, very stable and are evenly distributed in serum without clusters.

The nanocapsule can be readily endocytosed into the cytosol of target cells. Upon proteolytic cleavage of the cross-linker, the polymeric shell disintegrates and the protein is released in fully functional form to the interior of the target cell. The degradability of the polymeric shell can thus be tuned by the selected sequence of the cross-linker to respond to different proteases and can also be spatiotemporally controlled by using photolabile caged peptide sequences.

Accordingly, an aspect of the invention is to provide an intracellular delivery system that uses noncovalent encapsulation that can protect a target protein from aggregation, proteolysis and denaturation.

Another aspect of the invention is to provide a method for reversible disassembly of the protective layer and release of the target protein upon reaching the cellular target or on demand without diminishing the biological activity of the target protein cargo.

Another aspect of the invention is to provide an intracellular delivery system that provides increased efficiency in transport across cell membranes for proteins and drugs that have intracellular or nuclear targets.

A further aspect of the invention is to provide an enzyme specific cross-linker that can be used to both create and provide enzyme specific disintegration of a single cargo molecule nanocapsule.

Another aspect of the invention is to provide an intracellular delivery system that will successfully deliver both cytosolic and nuclear proteins in active forms to a variety of cell lines.

Another aspect of the invention is to provide an intracellular delivery system that will successfully deliver siRNA, plasmids and other small nucleic acids and parts in active forms to a variety of cell lines.

Still another aspect of the invention is to provide an intracellular delivery system that allows control over the timing, rate and location of capsule degradation and release of the cargo molecule into the target cell.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes one embodiment of the present invention is depicted in the methods generally shown in FIG. 1 through FIG. 6E. It will be appreciated that the methods may vary as to the specific steps and sequence and the apparatus may vary as to structural details, without departing from the basic concepts as disclosed herein. The steps depicted and/or used in methods herein may be performed in a different order than as depicted in the figures or stated in the text. The steps are merely exemplary of the order these steps may occur. The steps may occur in any order that is desired, such that it still performs the goals of the claimed invention.

The present invention provides methods for protease-mediated intracellular delivery of selected cargo contained in nanocapsules and for producing nanocapsules with protease specific degradation.

Figure 1:
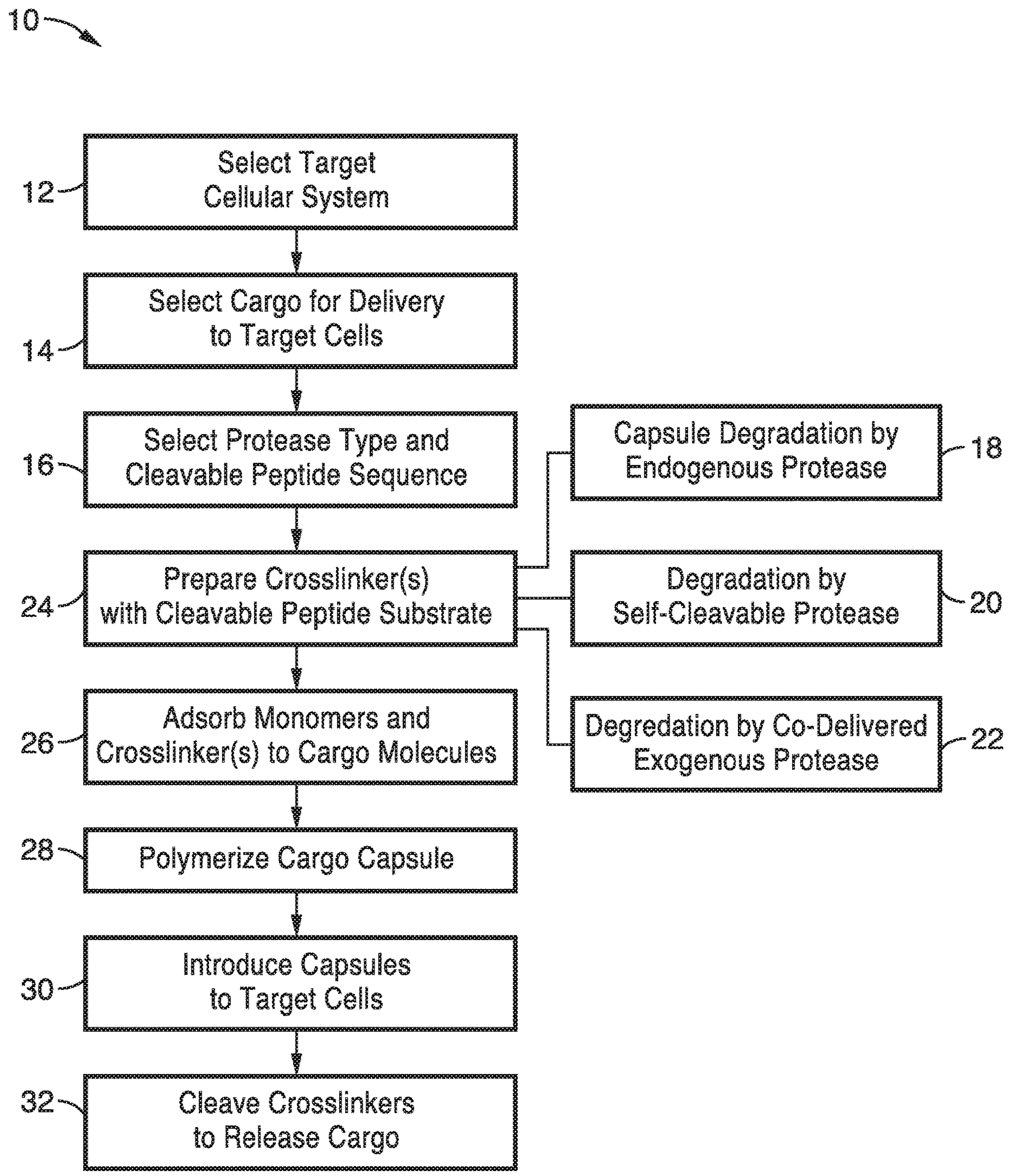
FIG. 1 is a flow diagram of a method for protease-mediated intracellular protein delivery with nanocapsules according to one embodiment of the invention.

Turning now to FIG. 1, the steps according to a preferred embodiment 10 of the present system and method for intracellular delivery of selected cargo molecules to a desired cellular system and for producing selectively degradable nanocapsules is illustrated. At block 12, a target cellular system is identified. It will be seen that the methods of the present invention can be applied in many different settings such as medical treatments, biological research, and diagnostic imaging, where intracellular delivery of functional molecules is needed. The methods are applicable to essentially every animal cell type and cellular system. The selection of the target may influence the selection of the cargo molecule at block 14 and the selection of the protease and substrate sequence at block 16. For example, a cancer therapy for a particular type of cancer may exploit cellular conditions that are characteristic of that cancer and may determine the identity of a delivered cargo protein or the protease and its substrate sequence. As illustrated in several of the examples, the protease furin is upregulated in several different carcinomas compared with normal cells. Therefore, furin-cleavable nanocapsules are a good candidate for use in designing and adapting the methods to a specific treatment scheme.

Once the target system is selected, the cargo for delivery to the target system is selected at block 14 of FIG. 1. The cargo can be biologically relevant proteins such as cytokines, transcription factors, signal proteins, enzymes, nuclear proteins, peptides as well as small drugs, and nucleic acids such as siRNA and plasmid DNA. The cargo could also be inert molecules to facilitate different types of imaging.

At block 16, the protease and the associated cleavable peptide sequence substrate are selected. There are three general approaches to this selection at block 16. These approaches are also shown schematically in FIG. 5A through FIG. 5C.

Figure 5A:
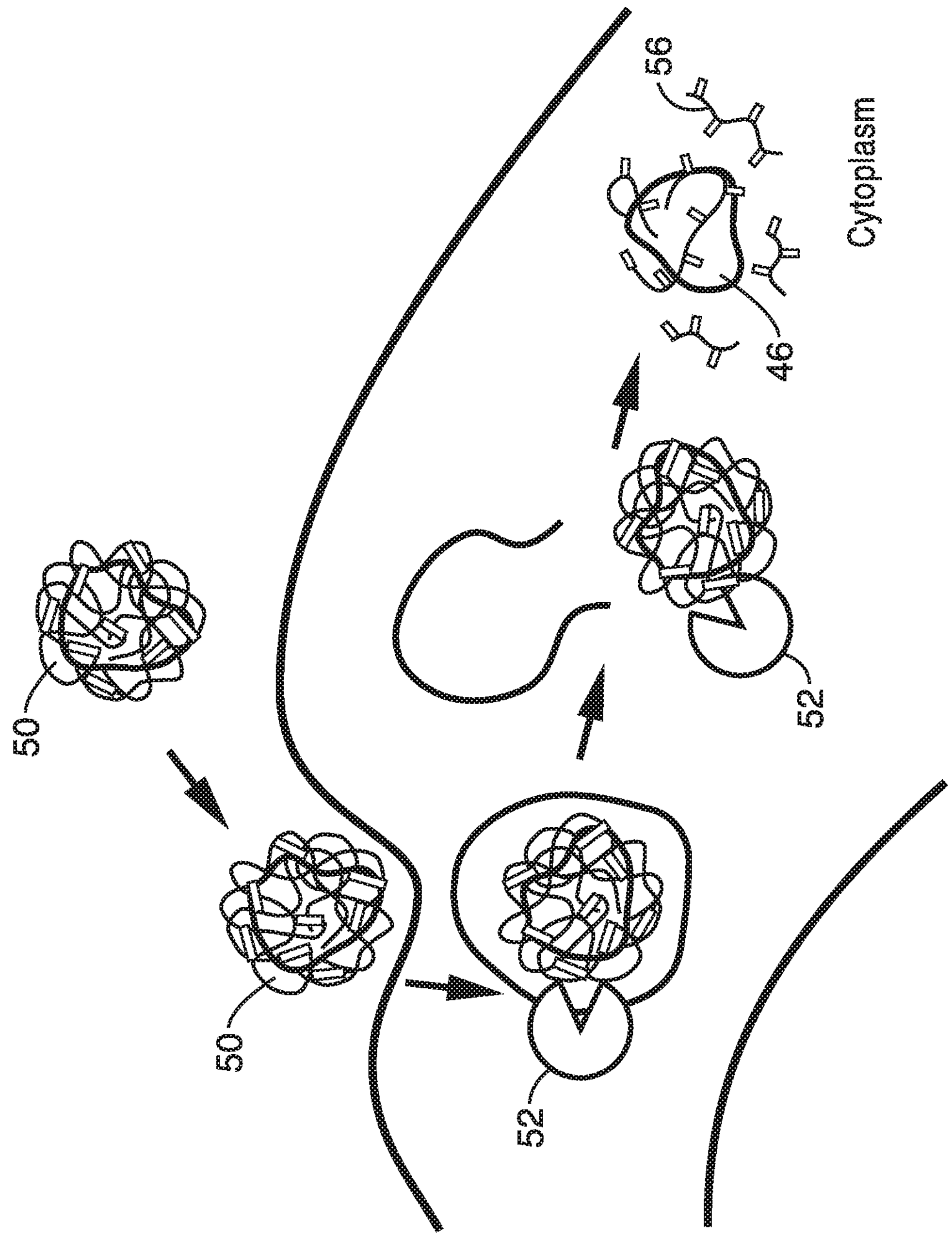
FIG. 5A-FIG. 5C are schematic diagrams of nanocapsule type selection for capsule degradation assisted by a) an endogenous protease; b) exogenous self-cleavable protease; or c) co-delivered exogenous protease (parallel delivery or binding delivery by a conjugate) according to the invention.

The first approach is to select at block 18 an endogenous protease that is found in the target cell as shown in FIG. 5A. In order to deliver a wide assortment of functional proteins that can interact with different cellular targets, a general mechanism for enzymatic degradation of the nanocapsule and release of the protein cargo is preferred. However, endogenous proteases specific to a target cell or location within a cell may also be selected.

One preferred general endogenous protease that can be selected to assist in the disintegration and release of delivered cargo from nanocapsules is the essential endoprotease furin (53 kDa), which is a ubiquitous proprotein convertase expressed in all eukaryotic organisms and many mammalian cells. Furin is localized in various intracellular locations and has a preferred substrate in the form RX(K/R)R↓ (R: arginine; K: lysine, X: any amino acid; ↓: the cleavage site). Furin processes a diverse group of endogenous proproteins and foreign proteinaceous substrates, including those from bacterial toxins, such as Shiga toxins and anthrax as well as many viruses, such as measles and HIV-1.

While furin is a preferred endogenous protease, it will be understood that other proteases and associated peptide sequences can also be used. For example, other proteases include enzymes categorized as aspartate proteases, cysteine proteases, glutamic proteases, metalloproteases, serine proteases, and threonine proteases.

Figure 5B:
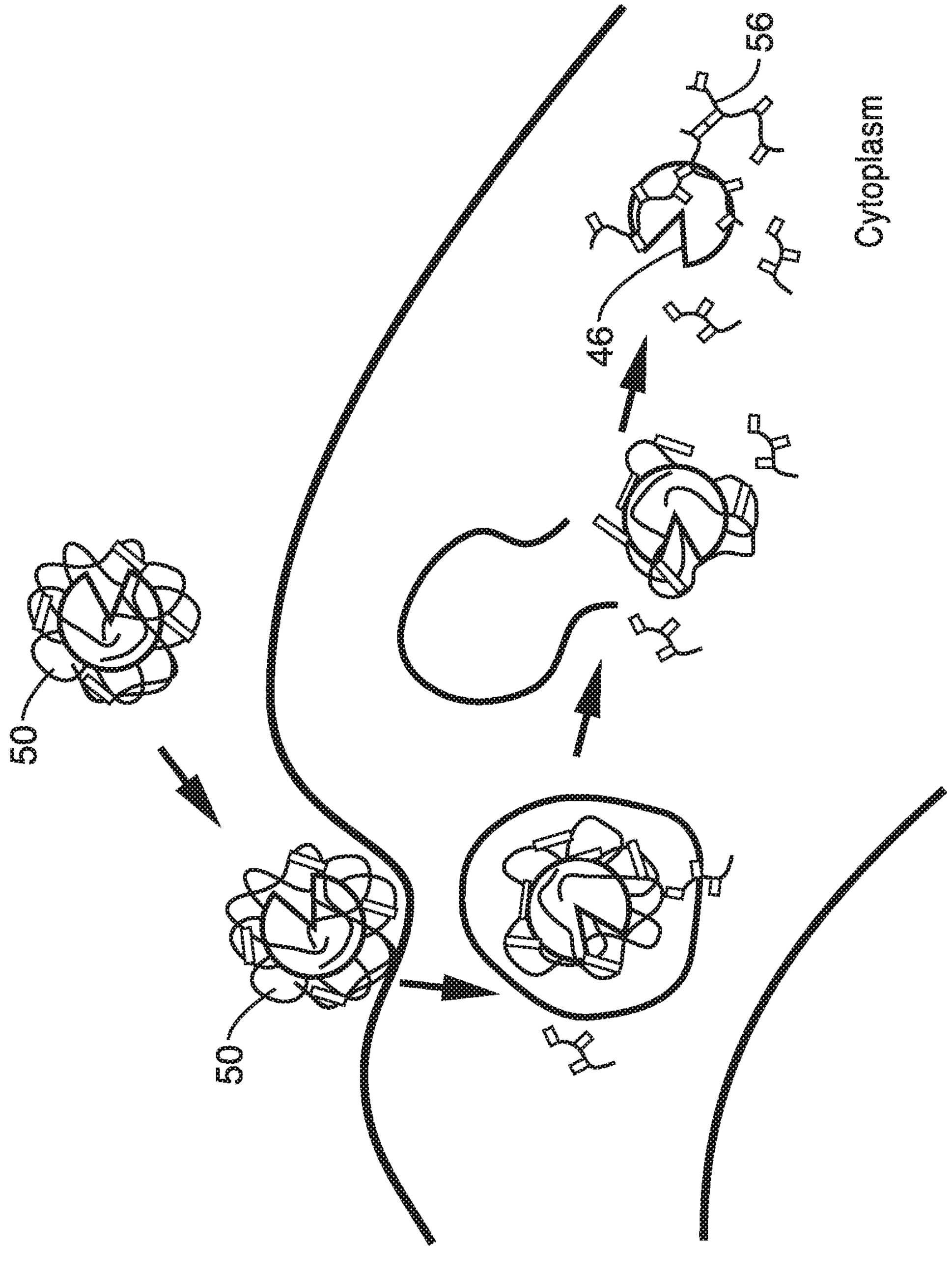

Alternatively, selected degradation of the delivered capsules can be by a self-cleavable peptidase at block 20 as illustrated schematically in FIG. 5B. One self-cleavable peptidase is mature caspase-3 and its use is illustrated in Example 1 herein. Degradation of the delivered capsule inside of a cell does not depend on the presence of any particular peptidases within the target cell in this embodiment.

Figure 5C:
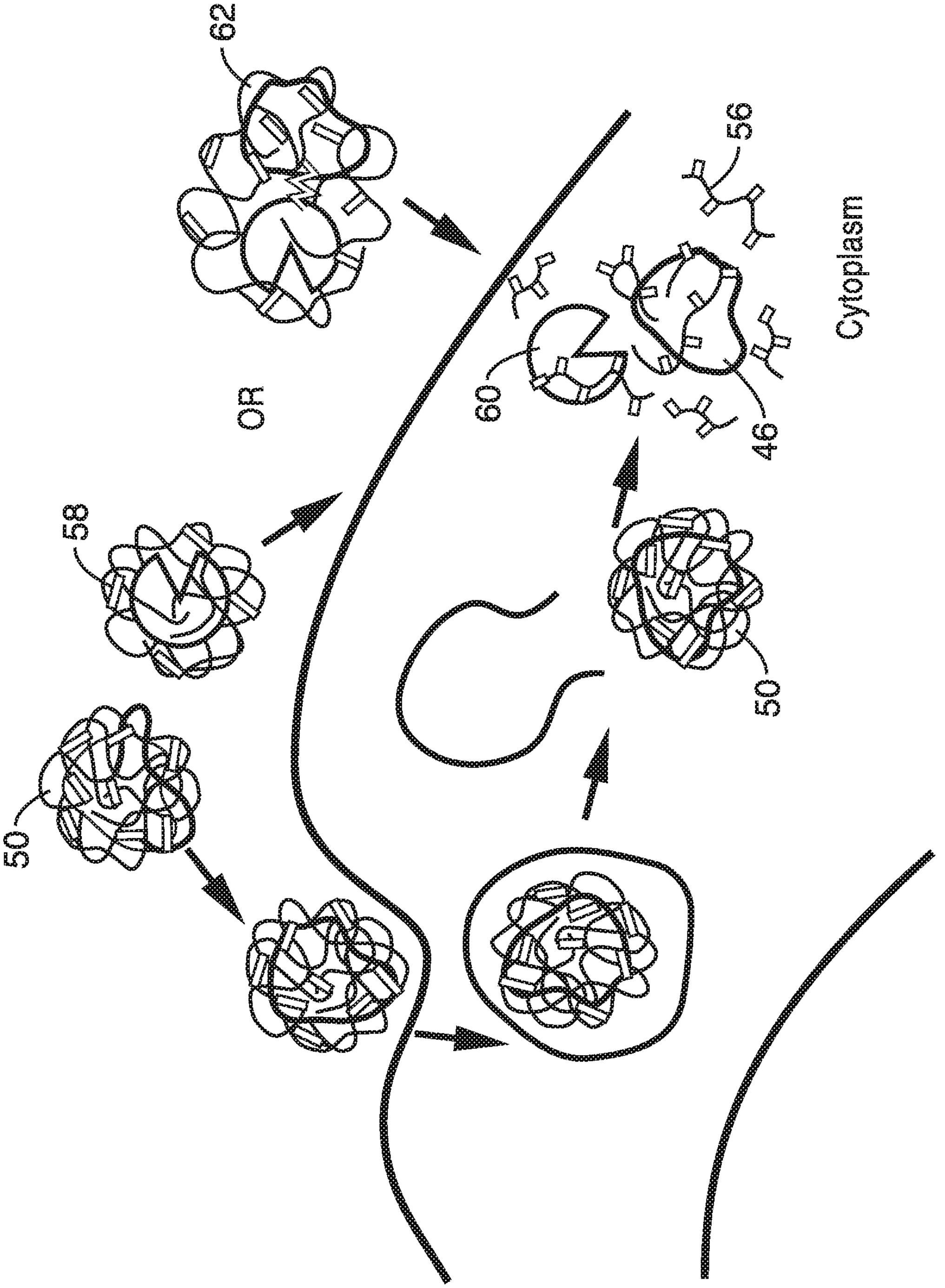
Figure 6A:
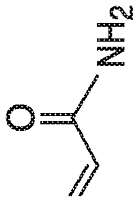
FIG. 6A through FIG. 6E are schematic diagrams of monomers and cross-linkers used for preparation of different caspase-3 containing nanocapsules as described in Example 1. M1: acrylamide; M2: N-(3-Aminopropyl)methacrylamide; CL1: N,N'-methylene bisacrylamide; CL2: acrylated VDEVDTK and CL3: acrylated VDVADTK (cleavage sites are identified by a dash line) according to one embodiment of the invention.
Figure 6B:
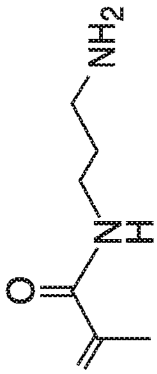
Figure 6C:
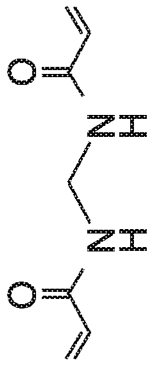
Figure 6D:
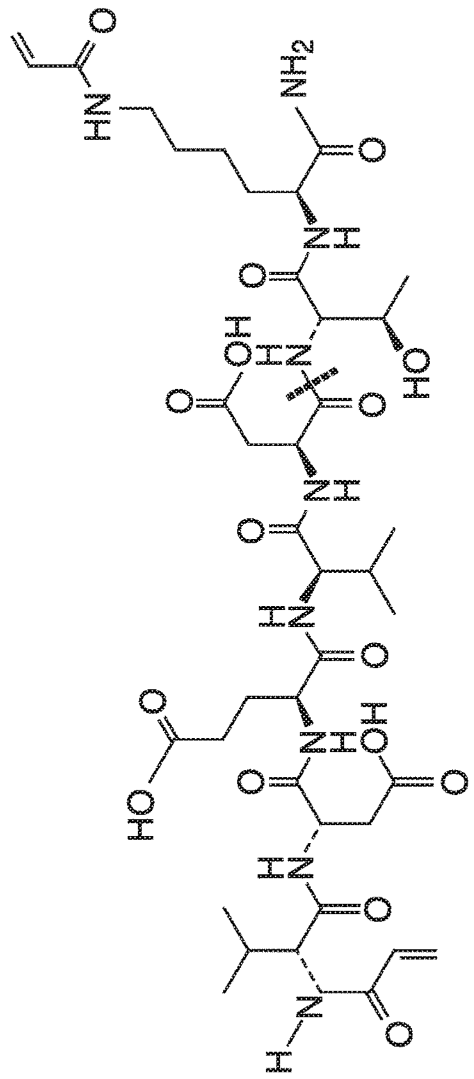
Figure 6E:
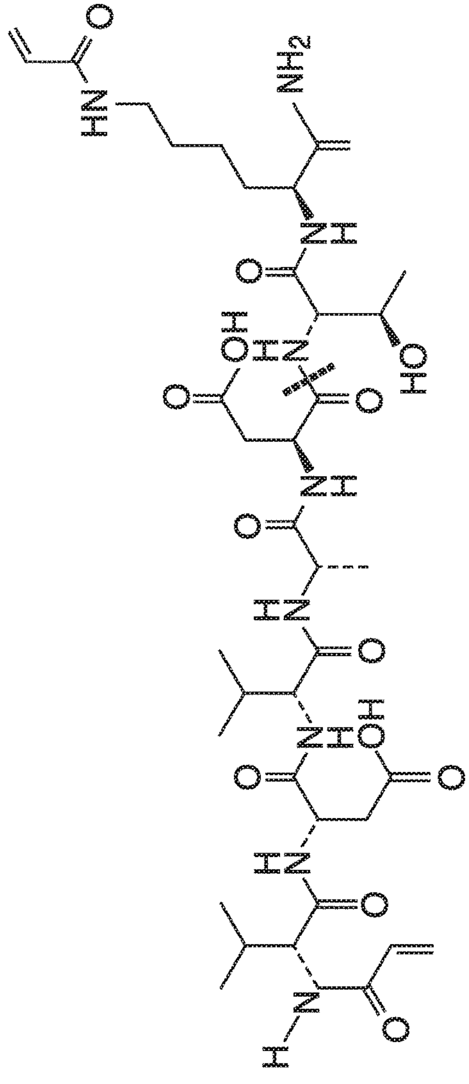

A third alternative protease selection scheme at block 16 is the parallel delivery of exogenous proteases at block 22 of FIG. 1. For example, one can co-deliver a recombinant target protein together with the exogenous protease encapsulated within nanocapsules that are cross-linked by the peptide substrate of the co-delivered protease, either by a parallel approach or a binding approach as shown in FIG. 5C.

Figure 2A:
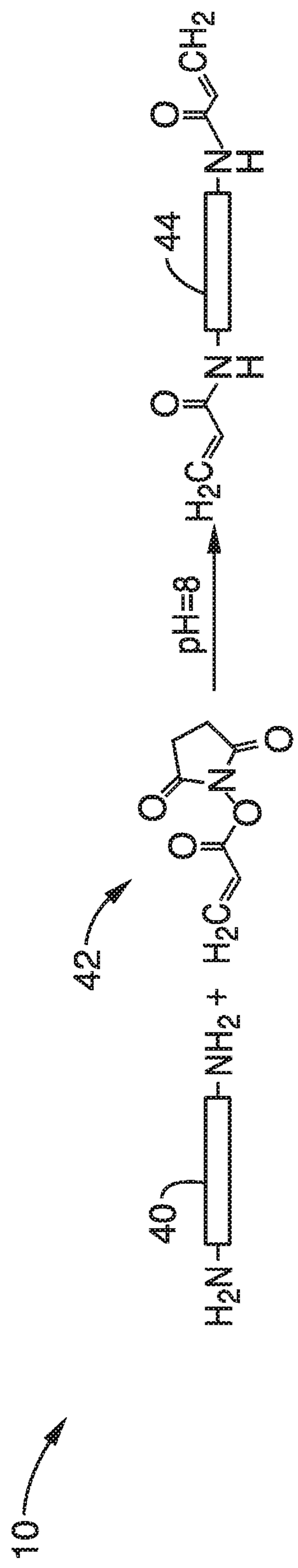
FIG. 2A and FIG. 2B are schematic diagrams of alternative cross-linker synthesis schemes of one embodiment of the method for protease-mediated intracellular protein delivery.
Figure 2B:
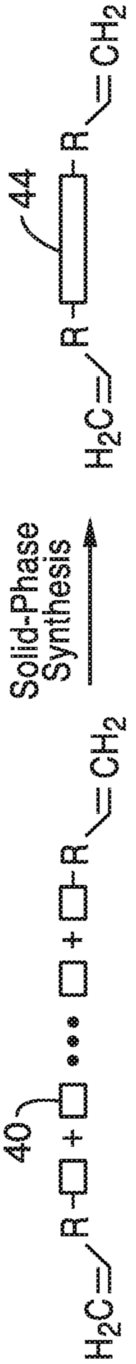

The selection of the protease at block 16 will direct the character of the associated substrate that is made part of the cross-linker construct. Normally the peptide sequence that is capable of being cleaved by the protease is selected. As illustrated in FIG. 2A or FIG. 2B, the cleavable peptide is incorporated into the structure of cross-linkers at block 24. The selected peptide can be synthesized or isolated by conventional methods.

The intracellular protein delivery scheme described in FIG. 1 is preferably based on the formation of a protein nanocapsule consisting of a single-protein core and a thin polymeric shell cross-linked by designed peptides, which can be specifically recognized and cleaved by a protease. Referring also to FIG. 2A, the polymerizable cross-linkers 44 with peptide sequences 40 are typically prepared by acryloylation with terminal free amine groups (i.e., free amine of N-terminus; free amine of lysine (K) positioned at C-terminus) via N-acryloxysuccinimide 42. Alternatively, the peptide 40 based cross-linker 44 can also be obtained by directly incorporating acrylate, vinyl or allyl modified amino acid during the peptide synthesis such as solid phase peptide synthesis as seen in FIG. 2B. Other methods for creating cross-linkers 44 with a cleavable substrate section or sections can also be used at block 24.

In the preferred embodiment, a one-pot procedure may be used for the preparation of protein nanocapsules, including protein-surface deposition with monomer(s) or cross-linker and in situ aqueous polymerization to individually encapsulate proteins as seen schematically in FIG. 2.

Figure 3:
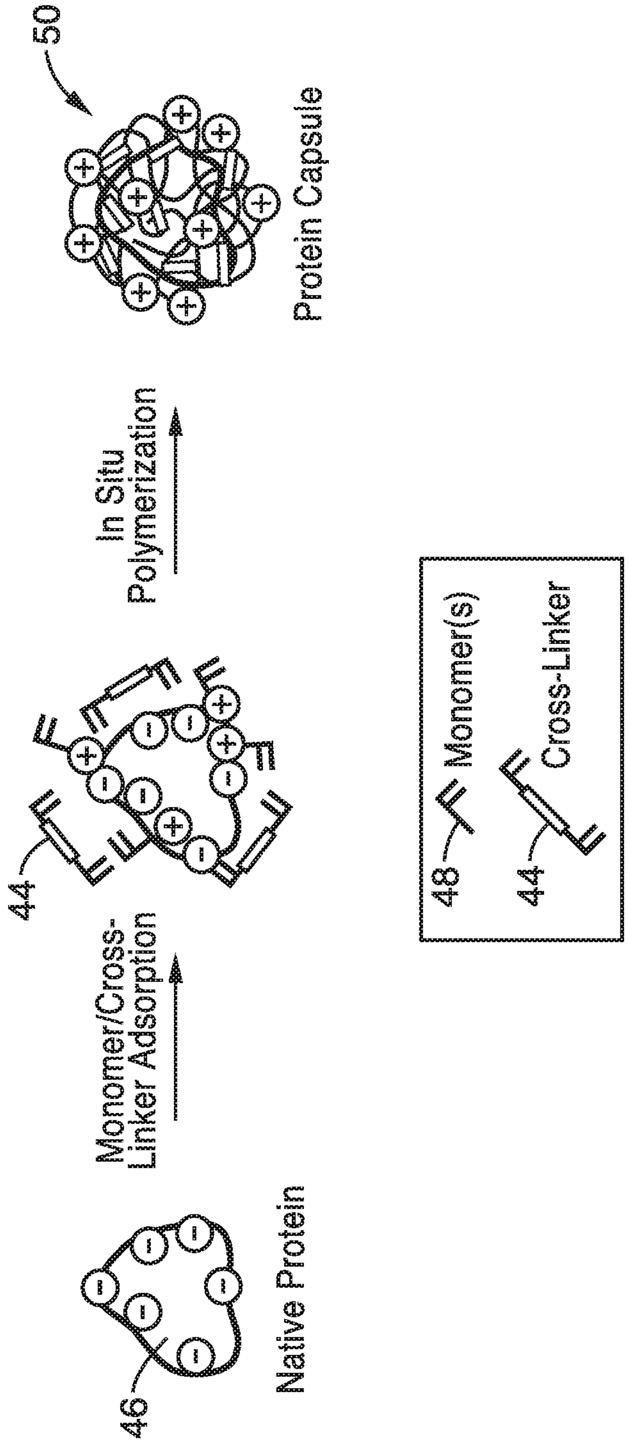
FIG. 3 is a schematic diagram of a synthesis scheme for enzyme cleavable cross-linked nanoencapsulation according to the invention.

At block 26 of FIG. 1 one or more monomer types and cross-linkers are adsorbed onto cargo molecules. As also shown in FIG. 3, the first deposition step is to self-assemble and concentrate the monomer(s) 48 and/or cross-linkers 44 to the surface of the target cargo protein 46 at a certain concentration (0.1-1 mg/mL) by electrostatic force based adsorption (e.g., if the protein is negatively charged at the pH value of the reaction buffer, positively charged monomers are used for self-assembly; while if the protein is positively charged, negatively charged monomers are involved). However, it is preferred that the final overall surface charge of the polymerized nanocapsule is positive to facilitate entry of the capsules into the target cells.

The second step is the in situ free radical polymerization in aqueous solution, during which the target protein 46 is encapsulated with the matrix of monomers 48 and cross-linkers 44 at block 28 and shown schematically in FIG. 3. In particular, it is preferred that positively charged monomers 44, such as those with amine groups are used during polymerization step so as to guarantee the final surface charge of the particles is positive, which is essential for the cell-membrane penetration. In this illustration, a positive surface charge on the nanocapsule 50 is desired to facilitate cellular entry by interaction with the negatively charged phospholipid bilayer membrane. Nevertheless, to achieve selective cellular uptake, targeted positive ligands could also be attached to the surface of the nanocapsules 50, and the surface charge could be adjusted to neutral by using uncharged monomers in that embodiment.

At block 30, nanocapsules 50 that are preferably small in size (sub-20 nm) and have a positively charged polymeric shell, proteins or other cargo 46 enclosed in the nanocapsules 50 can be efficiently delivered into cells. The resulting capsules 50 have been shown to have low toxicity, high cell penetration, long term stability, and even distribution in serum without clustering and are capable of being localized in the cell and specifically triggered by a selected protease.

Figure 4:
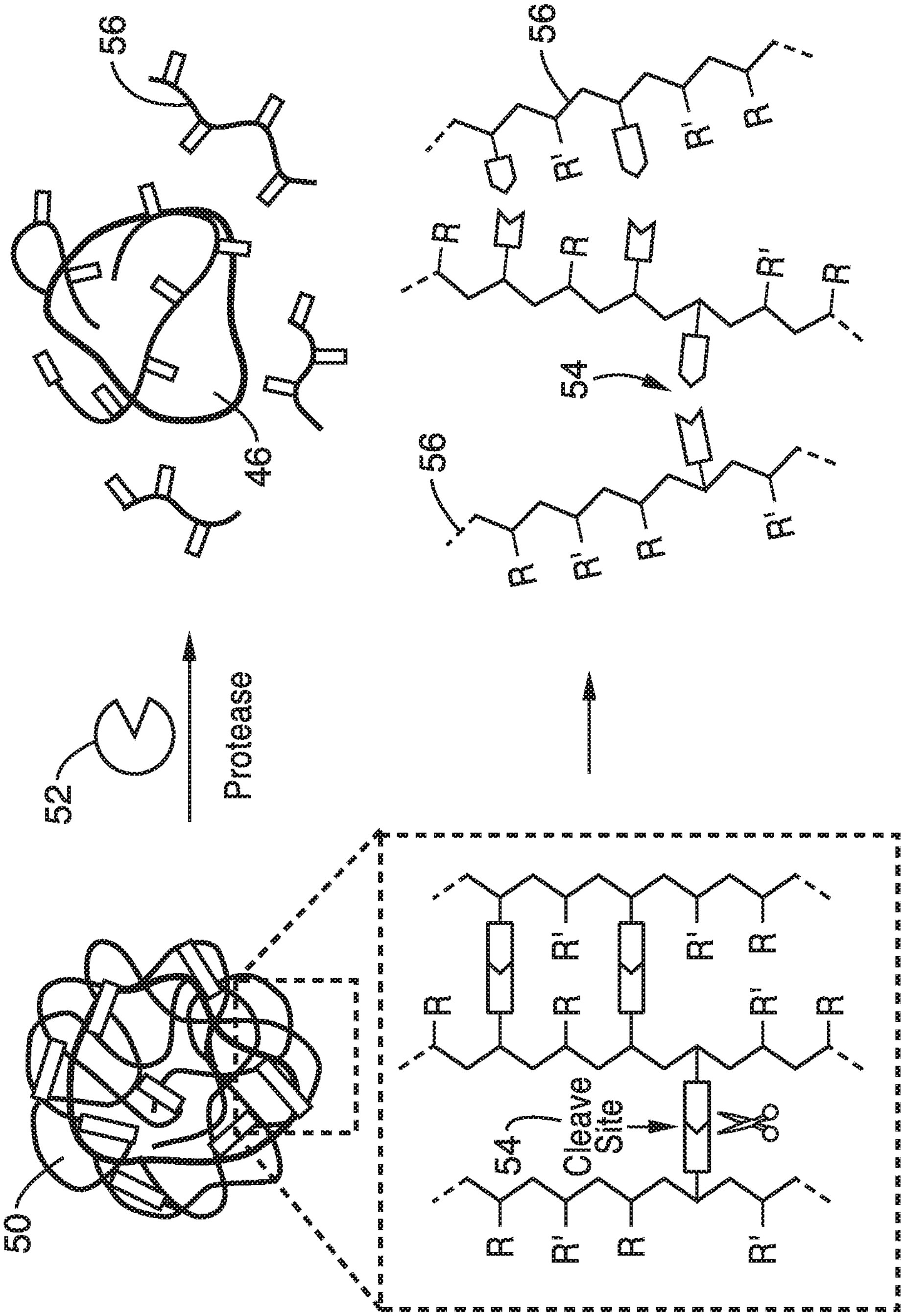
FIG. 4 is a schematic diagram of one release mechanism of a nanocapsule produced by the synthesis shown in FIG. 3.

As shown in FIG. 4, the polymeric shell of the protein nanocapsule 50 can then be digested by specific proteases 52 that are either expressed endogenously or supplied exogenously at block 32. The cargo 46 is released from the digested capsule 50 with the cleaving of cross-linker cleavage sites 54 of the polymerized shell. Cleavage of the cross-linker cleavage sites 54 by the site specific enzyme 52 will cause the protective capsule shell to break up into pieces 56 that disassociate and release the cargo molecule. Once the active sites of the delivered protein cargo are exposed, the functional activity of the cargo 46 will be observed in the target cell.

Referring specifically to FIG. 5A through FIG. 5C, three different encapsulation and cargo release schemes are illustrated. In the first scheme shown in FIG. 5A, the nanocapsule 50 containing the cargo 46 is formed with cross-linkers that have cleavage sites that can be cleaved by an endogenous protease 52 such as furin that is present in the cytosol of the target cells. The nanocapsules 50 are introduced into the target cell by endocytosis. The cargo molecule 46 is released by the activity of the specific endogenous protease 52 on the cross-linker substrate that results in breaking the capsule into pieces 56. This general scheme is illustrated in Example 2 through Example 5 below.

In the scheme shown in FIG. 5B, a nanocapsule is formed that contains a cargo molecule that is a protease. The cross-linkers of the nanocapsule 50 include cleavage sites that are specific to the protease cargo 46. Consequently, the capsules are self-degrading from within and the nanocapsules have a limited life span. The nanocapsule 50 is introduced into the cell by endocytosis. Eventually the protease cargo 46 is released into the cytosol and the released protease can cleave other nanocapsules releasing the contents. Caspase-3 is used in Example 1 to illustrate this scheme.

A parallel delivery scheme is shown in FIG. 5C. Nanocapsules 50 containing a cargo molecule and nanocapsules 58 containing a protease 60 are prepared. The two sets of nanocapsules are introduced to the target cell by endocytosis. The protease cargo nanocapsules either self-degrade or are prepared with cross-linkers with cleavage sites for endogenous proteases and the protease cargo is released. The released protease 60 degrades the other nanocapsules 50 by cleaving the cleavage sites that are specific for that protease 60 in the cross-linkers of the capsule 50 thereby releasing the cargo of nanocapsule 50.

Alternatively, a single capsule containing a protease and the target molecule is prepared as shown in FIG. 5C. The nanocapsule 62 containing the two can self degrade if the capsule has cross-linkers with cleavage sites for that protease or the nanocapsule 62 can be formed with cross-linkers that are cleaved by endogenous proteases.

To illustrate a parallel delivery scheme at block 22 of FIG. 1 and shown in FIG. 50C, nuclear localization signal (NLS) conjugated with enhanced green fluorescent protein (eGFP) was first cross-linked by the caspase-3 cleavable peptide VDVEDTK within the polymeric shell, which covers up the NLS peptide. Then the eGFP with embedded NLS was co-delivered to HeLa cells with the self-degradable caspase-3 nanocapsules described in Example 1. Once the delivered caspase-3 protease was released from the first capsules, the shell layer of eGFP is further digested, and the NLS peptide will be exposed and facilitate the eGFP penetration into the nucleus. In the absence of activated caspase-3, the eGFP can only be delivered into the cytosol. However, with the aid of co-delivered caspase-3, part of eGFP with released NLS can be found inside nuclei. This delivery strategy can be further used for the intranuclear delivery of transcription factors.

There are variations on the basic scheme described in FIG. 2 through FIG. 5 that are also useful. For example, more than one type of monomer can be used to form the nanocapsules. As illustrated in the Examples below, a first monomer type (acrylamide) and a second monomer type (N-(3-aminopropyl) methacrylamide) are both adsorbed to the cargo molecule and cross-linked. In another embodiment, the first monomer type adsorbs with the cargo molecules and the second monomer type couples with the first monomer type. The first monomer type acts as a reversible anchor or seed monomer for the second monomer and one or both of the monomers are then cross-linked in this embodiment.

Likewise, there can be variations in the number and type of cross-linkers that can be used. For example, the cross-linker construct can have several cleavage sites that can be cleaved by the enzyme that was selected at block 16 of FIG. 1 so that nanocapsule will be broken up into smaller fragments and be sensitive and functional with small concentrations of the selected proteases within the cell. In another embodiment, there is a first cross-linker construct with a first enzyme cleavage site and a second cross-linking construct with a second enzyme cleavage site. Release of the cargo is controlled by the activity of two different enzymes providing some control over the conditions of the release such as timing and rate of release in the target cell.

Further control over the release of the cargo molecule selected at block 14 can be exerted with the selection of cross-linkers and the parallel introduction of two types of nanocapsules. For example, a first nanocapsule is produced with the selected cargo molecule formed with monomers and cross-linkers that have an amino acid sequence that is specific for cleaving by a protease that is exogenous to the target cell. A second nanocapsule is produced containing a protease cargo molecule that will cleave the cross-linkers of the first nanocapsule and the second capsule has cross-linkers that will be cleaved by proteases that are exogenous to the target. Both nanocapsules are introduced to the target cell and the first nanocapsules are not degraded until the release of the exogenous protease cargo of the second nanocapsules.

Accordingly, it can be seen that the methods of the present invention can be adapted to deliver proteins and other sensitive cargo molecules to many different target cell types with the formation of a protease-degradable nanocapsules around the target protein, which are easily prepared by an in situ polymerization with enzymatically cleavable peptides and small monomers in aqueous solution.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the protease native protein delivery approach methods, the protein caspase-3 was selected for encapsulation with self-degradable and non-degradable cross-linked monomer capsules. The prepared capsules were delivered into HeLa cells and cell mortality was compared.

Caspase-3 (CP3) is a key executioner caspase for programmed cell death (apoptosis) and occupies a prominent position in the apoptotic cascade where death signals from both of the intrinsic and extrinsic stimuli converge to activate downstream death events. Successful cytoplasmic delivery of functional CP3 can therefore lead to cell apoptosis and therefore apoptosis is an indicator of CP3 delivery.

Typically, caspase-3 exists in normal cells as an inactive zymogen and must be activated by proteolytic processing during the apoptosis pathway. However, for this illustration mature caspase-3 rather than the procaspase was obtained after overexpression in transformed *Escherichia coli* BL21 (DE3) and was purified using a nickel-resin affinity column.

Two cross-linkers with peptide sequences VDEVDTK and VDVADTK were designed with the substrate of caspase-3 DEVD and VDVAD respectively. CP3 specifically cleaves a peptide with the sequence Asp-Glu-Val-Asp (DEVD) after the second aspartic acid. Therefore, the nanocapsules will be cross-linked with a cross-linker that includes a CP3 cleavable peptide and will be essentially self-degradable. Accordingly, the mature CP3 was encapsulated in a DEVD-cross-linked polymeric shell that can be degraded by CP3 from within. Each peptide cross-linker was terminally conjugated with reactive acrylate groups by N-acryloxysuccinimide.

The monomers and cross-linkers used for preparation of caspase-3 nanocapsules in this example are illustrated schematically in FIG. 6A through FIG. 6E. These illustrative monomers are designated as M1: acrylamide and M2: N-(3-Aminopropyl)methacrylamide and the cross-linkers CL1: N,N'-methylene bisacrylamide; CL2: acrylated VDEVDTK; and CL3: acrylated VDVADTK (cleavage sites are indicated with a dashed line).

To encapsulate CP3 within a nanocapsule, in situ radical polymerization at 4° C. was performed in the presence of (1) mature CP3; (2) two monomers, acrylamide (AAm) and N-(3-aminopropyl) methacrylamide (APMAAm), which create a positively charged surface that can improve cell-penetrating efficiency, and a bisacryloylated VDEVDTK peptide as cross-linker (VDEVDTK). The low temperature process was selected to ensure the level of proteolysis by CP3 is minimized during the polymerization process.

As indicated above, the polymeric shells of the caspase-3 nanocapsules were formed by radical copolymerization, which occurred around the protein surface with a pre-adsorption treatment by monomers with the opposite charge to the protein. Purified caspase-3 was diluted to 1 mg/mL with 20 mM pH 8.5 bicarbonate buffer. Specifically, a certain amount of acrylamide (M1) aqueous solution with a concentration of 200 mg/mL was added to 3 mL protein solution with stirring for 10 minutes at 0-4° C. Subsequently, the other positively charged monomer N-(3-Aminopropyl) methacrylamide (M2) was added with stirring for another 10 minutes.

Thereafter, the cross-linkers were added to each solution. To form non-degradable coatings, N,N'-methylene bisacrylamide (CL1) was added. For degradable coatings, VDEVDTK or VDVADTK cross-linkers were added. The M1/M2/cross-linker molar ratio of 8/6/1 was used. The polymerization was immediately initiated by adding 3 mg of ammonium persulfate dissolved in 30 μL of deoxygenated and deionized water and 3 μL of N,N,N',N'-tetramethylethylenediamine into the test tube. The reaction was allowed to proceed for 60 minutes in a nitrogen atmosphere. Finally, buffer exchange with 100 mM pH 7.4 phosphate solution was carried out with a Millipore filter to remove monomers and initiators.

The size of nanocapsules could be adjusted by varying the amount of monomers/cross-linker to protein. With a fixed ratio of (8/6/1) for AAm/APMAAm/VDEVDTK, the sizes of the resulting nanocapsules could be fine-tuned between 8 nm and 20 nm by varying the ratio of protein to monomers. Specifically, when the molar ratio of protein to AAm was 1:1200, the average hydrodynamic radius of the resulting CP3 nanocapsules was ~13 nm. In contrast, the size of native CP3 protein was ~5 nm.

Analysis of the free and the caspase-3 nanocapsules confirmed that the protein encapsulated inside the nanocapsule retained its secondary structure.

Evaluation of the in vitro activity was conducted by using a colorimetric substrate Ac-DEVD-pNA (p-nitroanilide), which can be cleaved by caspase-3, and the amount of product pNA can be monitored at 409 nm over time. The continuous self-degradation process was dynamically monitored by measuring the average count rate by DLS. In contrast to the native protein, caspase-3 nanocapsules showed distinct activity curves indicative of a two step process. There was an initial lag phase (30 min) in which digestion of the external substrate was slow, was followed by a linear phase parallel to that of the native CP3 reaction. Presence of the distinctive lag phase is suggestive of an initial period in which CP3 digests the DEVD cross-linkers and becomes liberated from the nanocapsule. The activity of CP3-nanocapsules was dramatically attenuated at 4° C., indicating limited self degradation of the polymer shell at that temperature. Taken together, these results demonstrate the importance of the peptide cross-linker in modulating nanocapsule degradability.

Intracellular delivery of the different caspase-3 nanocapsules was carried out in HeLa cells. Cytotoxicity tests were determined by the 3-[4,5-dimethylthiazol-2-yl]-2,5-diphenyl tetrazolium bromide (MTT) assay. Cell viability after treatment with native CP3 protein and protein nanocapsules with different particle sizes, as well as different cross-linkers was evaluated. Delivered CP3 activity was determined by the appearance of apoptotic indicators such as membrane blebbing and cell shrinkage and these were clearly observed in HeLa cells treated with 200 nM CP3-nanocapsules for 24 hours.

In contrast, native caspase-3 did not exhibit obvious cytotoxicity, which was not surprising since the caspase-3 protein was unable to enter the cells without a transport carrier. Additionally, in the absence of the protective polymeric shell, the native caspase-3 was quickly denatured in the serum-containing medium.

A comparison of two nanocapsules of different sizes that were obtained via different synthesis ratios of protein/monomer was made and these provided different toxicity results. Although both capsule sizes exhibited significant cytotoxicity, the smaller capsules showed a lower $IC_{50}$ (below 100 nM). This can be attributed to a more rapid self-degradation process that benefited from a thinner polymeric shell that contained less monomer and cross-linker.

Furthermore, non-degradable caspase-3 nanocapsules cross-linked by N,N'-methylene bisacrylamide (CL1) showed insignificant cytotoxicity compared with capsules cross-linked by the cleavable peptides. It has been shown that caspase-3 has more efficient hydrolysis of the substrate sequence DEVD than for the sequence VDVAD. Predictably, nanocapsules cross-linked by DEVD showed a lower $IC_{50}$ (below 100 nM) than capsules cross-linked by VDVAD (ca. 400 nM).

Overall, it was seen that the self-degradable caspase-3 nanocapsules inhibited the proliferation of HeLa cells dramatically as compared with the control groups, including native protein and non-degradable nanocapsules. In particular, the nanocapsules with a mean diameter of 8 nm exhibited a pronounced inhibitory effect that the treatment of caspase-3 at 200 nM induced an over 90% reduction in the cell growth, whereas free protein alone and protein encapsulated in the non-degradable shell did not show a conspicuous inhibitory effect. It was further evident that the induced HeLa apoptosis is mediated through a caspase-3-released pathway mediated by the degradation of the nanocapsules.

Example 2

Noncovalent encapsulation of a target protein cargo in a thin positively charged monomer layer using two monomers and furin-cleavable peptides as cross-linkers was conducted to illustrate the broad capabilities of the method. In this example, the peptidyl cross-linkers are analogous to various furin substrates within a cell. Upon entry into the cell, where furin activities are abundant at various intracellular locations, the capsules are proteolyzed and the polymeric matrix degrades, leading to the release of the cargo molecule in native form.

A highly favored furin substrate (RVRR) was selected as a cleavage site and a bisacrylated peptide (Ahx-RVRRSK) as the nanocapsule cross-linker was synthesized. Fmoc chemistry was used to synthesize a peptide with 6-aminohexanoic acid (Ahx) at the N-terminus and a methyltrityl (Mtt)-protected lysine residue at the C-terminus. After selective deprotection and cleavage of the Mtt protection group with 3% trifluoroacetic acid (TFA), the peptide was bisacrylated using acryolyl chloride. This strategy, which utilized differential acid-labile protection groups on the side chains of amino acids to synthesize the cross-linker, allowed acryolation of only the N- and C-terminal free amine groups while preserving the arginine groups unmodified for furin recognition. Additionally, complete synthesis on amide resin resulted in high yield and purity of the final peptide product. The cross-linkers were purified with high-performance liquid chromatography (HPLC) and characterized by liquid chromatography mass spectrometry (LCMS) analysis. Upon incubation with 1 unit of furin, complete cleavage of 1 ng of peptide was observed within 2 hours.

To prepare the protein-containing nanocapsules, monomers acrylamide (AAm) and positively charged N-(3-aminopropyl) methacrylamide (APMAAm) and the cross-linkers were first physically adsorbed onto the surface of the target proteins, which included enhanced green fluorescence protein (eGFP), caspase-3 (CP3), bovine serum albumin (BSA), or the transcription factor Klf4, in this example. This was followed by in situ free radical interfacial polymerization to form the polymeric shell and to assemble the nanocapsules, which can disintegrate and release cargo upon furin cleavage. Specifically, 1 mg of selected protein was diluted to 1 mL with 5 mM pH 9 $NaHCO_3$ buffer after which acrylamide (AAm) was added with stirring for 10 minutes at 4° C. Next, N-(3-aminopropyl) methacrylamide (APMAAm) was added. Afterward, the peptide cross-linker or nondegradable cross-linker N,N'-methylene bisacrylamide was added. The molar ratio of AAm:APMAAm:CL was 6:3.5:1. The polymerization was immediately initiated by adding 3 mg of ammonium persulfate and 3 μL of N,N,N',N'-tetramethylethylenediamine. The polymerization was allowed to proceed for 90 min at 4° C. Finally, buffer exchange with 100 mM 4-(2-hydroxyethyl)-1-piperazineethanesulfonic acid (HEPES) and 1 mM $CaCl_2$, pH 7.5, was performed to remove unreacted monomers and initiators.

The sizes of the resulting nanocapsules were assessed to be between 10 nm and 15 nm by dynamic light scattering (DLS). The nanocapsules also displayed a positive ζ potential of 7-9 mV, which is desirable for enhanced intracellular uptake.

Evaluation of the synthesized nanocapsules by transmission electron microscopy (TEM) revealed that the furin-degradable eGFP nanocapsules initially had a compact, spherical shape but after a 10 hour incubation with furin, the nanocapsules appeared completely dissociated, and were indistinguishable from native eGFP. Analysis of circular dichroism (CD) spectra also indicated that the secondary structure of eGFP remained unchanged during the entire nanocapsule assembly and disintegration process.

The release of eGFP from nanocapsules was quantified using the enzyme-linked immunosorbant assay (ELISA), since only released native eGFP is able to bind to anti-GFP antibody, while encapsulated eGFP is unable to be recognized by the antibody. In the absence of furin, degradable nanocapsules did not display significant protein release over a period of 24 hours, which was comparable to that of the nondegradable nanocapsules. This indicated that eGFP can remain encapsulated in the polymeric shell over an extended period of time and that protein diffusion effects are negligible. In addition, the nanocapsules did not show significant protein release in either acidic pH 5.5 buffer or a high-salt concentration, indicating the capsule remains intact and is not subject to nonspecific acid hydrolysis or destabilization due to shifts in ionic strength. These combined results confirmed that the release of native eGFP from the nanocapsules was specifically dependent on the enzymatic activities of furin.

Example 3

Having established the furin-dependent degradability of the nanocapsules, the ability of nanocapsules to deliver native proteins to the nuclei of mammalian cells was demonstrated in Chinese Hamster Ovary cell lines. The first target protein chosen was eGFP fused with the nuclear localization signal (NLS, sequence PKKKRKV) from the simian virus 40 large-T antigen (NLS-eGFP). NLS-eGFP was chosen as a fluorescent marker because the nanocapsule-mediated delivery into the cytosol of cells can be readily visualized. Furthermore, in the absence of capsule degradation, the NLS tag will be concealed and thus confine the eGFP fluorescence to the cytosol. Following furin-mediated degradation of the capsules, a release of NLS-eGFP is expected along with the subsequent entry of eGFP into the nucleus over time facilitated by the exposed NLS tag. The change in the localization of the eGFP signal will then be an indication of the release of protein cargo.

The extent of nuclear colocalization of delivered NLS-eGFP using different Chinese hamster ovary (CHO) cell lines with varied intracellular furin levels were compared, including CHO-K1 that expresses furin at a normal level, FD11 that is furin-deficient, and FD11+ furin which is the FD11 strain transfected with an overexpressed furin gene. Intracellular delivery of 200 nM furin-degradable NLS-eGFP nanocapsules that were incubated with CHO cell lines was examined with confocal microscopy after 24 hours. Localization of eGFP signal to the nucleus was prominent with furin-degradable nanocapsules in CHO-K1 and FD11+ furin cells. In contrast, eGFP fluorescence was only localized in the cytosol in FD11 cells, and no nuclear entry was observed, indicating no capsule degradation in the absence of furin. Furthermore, when non-degradable nanocapsules were used as delivery vehicles for NLS-eGFP, nearly all fluorescence was found only in the cytosol for all cell lines, confirming the inaccessibility of the encapsulated NLS-eGFP toward the nuclei.

To quantify the extent of nuclear delivery of NLSeGFP, the nuclear fractions from these treated cells were isolated and the amount of eGFP was measured using ELISA. The levels of eGFP delivered to the nuclei by furin-degradable nanocapsules were two to three times greater in furin-expressing cell lines compared to FD11. When these cells were co-cultured with furin-degradable NCs and 25 μM dec-RVKR-cmk, the amount of eGFP in CHO-K1 decreased to that of the FD11 levels.

The delivery of NLS-eGFP nanocapsules to human HeLa cell lines was also studied by the above microscopy and ELISA experiments, which demonstrated the same results as in CHO cells. Cellular trafficking studies with HeLa cells indicated that eGFP nanocapsules traffic through early endosomes and colocalization of nanocapsules with early endosomal marker, EEA1, peaked at ~60% after 30 minutes incubation. A decreased degree of colocalization after 60 minutes and 120 minutes of incubation may be attributed to the release of nanocapsules or protein from early endosomes into the cytosol. Notably, the lack of significant colocalization with late endosomal marker CI-MPR suggests that late endosomes are not involved in the internalization of these nanocapsules As controls, nearly no nuclear localization of eGFP was observed in: (1) NLS-eGFP delivered by nondegradable nanocapsules; (2) untagged eGFP delivered by furin-degradable nanocapsules; and (3) NLS-eGFP delivered by nanocapsules cross-linked with Ahx-AAARSK, which is not recognized by furin. The absence of nuclear eGFP delivery when nanocapsules were cross-linked with a nonfurin-specific peptide indicates that the peptide cross-linker is not subjected to hydrolysis by nonspecific proteases. Examination of furin-dependent nuclear delivery of eGFP utilizing: (1) CHO cell lines with varying furin concentrations; (2) a competitive furin inhibitor dec-RVKRcmk; and (3) nonspecific peptide cross-linkers (Ahx-AAARSK) collectively indicated that the presence of active intracellular furin and furin-degradable nanocapsules are both required for successful delivery.

Notably, the nanocapsules did not show significant cytotoxicity up to ~2 μM in cell lines treated with NLS-eGFP nanocapsules for 24 hours. Furthermore, FD11 and FD11+ furin cells treated with 400 nM furin degradable NLS-eGFP nanocapsules displayed identical cell morphologies and no visible toxicity despite different intracellular eGFP localization, further confirming the nontoxic nature of this delivery method. Thus, proteolytically cleavable nanocapsules can be constructed with specific peptide cross-linkers, and the degradation to release protein can be modulated by the activities of furin or other target endoproteases.

Example 4

Internalization of protein nanocapsules in various human cell lines was conducted to further illustrate the methods. Delivery of furin-degradable NLS-eGFP nanocapsules to the HeLa cell line, which exhibits high levels of furin expression, demonstrated significant eGFP localization within the nuclei. Quantitative analysis of nuclear eGFP levels also confirmed the successful delivery of eGFP to HeLa cells using furin-degradable nanocapsules.

Cellular trafficking of furin-degradable NLS-eGFP nanocapsules in HeLa cells was also explored. The eGFP fluorescence following nanocapsule incubation with cells for 2 hours was monitored by staining of early endosomal marker, EEA1, or the late endosomal marker, CI-MPR.

After a 30 minute incubation, eGFP nanocapsules showed ~60% peak colocalization with EEA1 indicating that the nanocapsules are internalized by endocytosis. The observation of eGFP fluorescence signals at later time points lacking colocalization with either endosomal marker indicates that some capsules or proteins are able to be delivered into the cytosol within 2 hours of cellular uptake. The inefficient escape of protein from the endosome to the cytosol remains an obstacle in many current delivery approaches. Delivery methods that rely on cytosolic esterases or reducing environments to release protein may never reach the cytosol and become entrapped in endosomes, undergo lysosomal degradation, and are eventually cleared from the system.

HeLa cells were also used to observe the effects of using various amounts of furin-degradable cross-linkers to synthesize nanocapsules. For example, the molar ratio of AAm:APMAAm:CL was varied from 6:3.5:1 (A) to 6:3.5:0.5 (B) and synthesized furin-degradable NLS-eGFP nanocapsules. Both nanocapsules that were produced had similar size and charge.

Cells treated with nanocapsules synthesized with relatively more cross-linkers (NC A) displayed higher colocalization with nuclei than those treated with NCs synthesized with less cross-linkers (NC B), while the overall internalization of eGFP and cell morphologies were comparable after 24 hours. When the nuclear fractions were extracted and eGFP was quantified with ELISA, nuclear eGFP of NC A-treated cells were significantly higher than that of cells treated with NC B. These results imply that the degradability and the surface chemistry of nanocapsules may play an important role in internalization and may facilitate cytosolic native protein delivery at various cellular entry points.

Protein delivery into human amniotic fluid-derived cells (hAFDCs) was also conducted. hAFDC cell lines have the potential to differentiate into all three germ layers and act as somatic resources which can be efficiently induced into a pluripotent state. Hence, controlled delivery of various factors to tune the functions of these cells has significant therapeutic potential. Both furin-degradable and nondegradable NLSeGFP nanocapsules were delivered to hAFDCs and examined the extent of nuclear delivery using confocal microscopy. hAFDCs treated with 200 nM furin-degradable nanocapsules show a marked overlap between cell nuclei and protein, while fluorescence signals from nondegradable nanocapsules were only detected in the cytosol.

After demonstrating the utility of nuclear eGFP delivery using a furin-mediated approach, delivery of transcription factors necessary to induce pluripotency was conducted. A transient transfection assay was first established with human 293T cell lines to monitor the activation of a human OCT4 promoter-driven luciferase (hOCT4-luc) construct. This hOCT4-Luc has been shown to be activated in iPS cells, presumably reflecting on the combined activity of OCT4, NANOG, SOX2, KLF4 and other potential regulators. By transient co-transfection of hOCT4-luc in 293 cell with constructs encoding one of the four iPS transcription factors such as pMXs-Oct4, or pMXs-Sox2, or pMXs-Klf4, or pMXs-c-Myc), we found that this promoter can be most efficiently activated by KLF4. Based on this result, experiments were conducted to compare the activity of native KLF4-11R protein and nanocapsulated KLF4-11R in transcriptional activation of hOCT4-luc. These results strongly indicate that furin-degradable nanocapsules can be used to deliver proteins to the nuclei of a diverse variety of mammalian cells.

Example 5

To further demonstrate the utility of furin-mediated release of functional protein cargo from the degradable nanocapsules, nanocapsules containing caspase-3 (CP3) were prepared with furin-cleavable peptide cross-linkers for delivery of caspase-3 to HeLa cells. These results were generally compared with the previous results of delivery of CP3 to cells using self-degradable nanocapsules cross-linked with CP3-cleavable peptides in Example 1.

CP3 is a potent executioner when delivered in native form to cells, as it acts as a signal peptidase in the cellular apoptotic pathway. Therefore, cell apoptosis is the physiological change observed upon successful delivery and release of native CP3 protein. CP3 nanocapsules were prepared in similar fashion as the eGFP nanocapsules of Example 4 starting from purified, recombinant CP3. Various control CP3 nanocapsules were also synthesized to facilitate comparison to the furin-degradable vehicle.

After confirmation of surface charges and sizes, the CP3 nanocapsules were added to HeLa cells. Cell death was only observed in HeLa cells treated with furin-degradable CP3 nanocapsules, with $IC_{50}$ of ~400 nM. In contrast, cells treated with unencapsulated native CP3, nondegradable nanocapsules, and furin-degradable bovine serum albumen nanocapsules controls all exhibited minimal apoptotic death within the concentrations of nanocapsules used, confirming the furin-dependent release of CP3 and the relatively non-toxic nature of the polymeric capsule. This indicates that only furin degradable CP3 nanocapsules are able both to enter the cell and to be degraded to release the executioner protein which can induce apoptosis.

To confirm the cell death observed was indeed apoptosis, a terminal deoxynucleotidyl transferase dUTP nick end labeling (TUNEL) assay which detects DNA fragmentation by labeling the terminal end of nucleic acids was performed. When cells were treated with 200 nM CP3-nanocapsules or protein, trademark cell membrane blebbing and shrinkage characteristics of apoptotic cells were observed in cells treated with furin-degradable CP3 nanocapsules. After detachment of cells and performance of the TUNEL assay, detection of DNA nicks observed with AlexaFlour488-labeled antibody were only detected in cells treated with furin-degradable CP3 nanocapsules. In contrast, native CP3-treated cells or nondegradable CP3 nanocapsule-treated cells did not show signals of nicked DNA in the total DNA content visualized with propidium iodide. This indicated that furin-degradable nanocapsules are able to deliver active CP3 to the cytosol and lead to apoptosis.

The successful delivery of CP3 also implicates the future potential of this system to deliver various cancer therapeutics which can interact with cellular machinery to activate the apoptotic pathway. The amount of furin-degradable cross-linkers incorporated in the nanocapsule can be tuned to achieve cell-specific intracellular protein delivery, as furin is upregulated in breast, ovary, head and neck, and brain as well as nonsmall cell lung carcinomas, in comparison to normal cells.

Example 6

To further demonstrate the delivery of biologically relevant nuclear protein cargos to different cell types, furin-cleavable nanocapsules encapsulating the transcription factor Klf4 were prepared for introduction into mouse embryo fibroblast (MEF) cells. The transcription factor Klf4 is critical in regulating expression levels of genes involved in maintaining the cell cycle as well as cellular structure, adhesion, metabolism, and signaling. Many studies implicate Klf4 as a tumor suppressor for colorectal and gastric cancers. In particular, Klf4 has been shown to be one of the essential factors needed to maintain a pluripotent state.

Recently, recombinant iPS transcription factor proteins were fused to protein transduction domains (PTDs) of multiple arginines (9R or 11R), transduced into mouse and human fibroblasts, and reprogrammed to produce induced pluripotent stem (iPS) cells. The 11R-tagged proteins have been delivered in vitro and in vivo to subcellular compartments, such as nuclei and mitochondria in a variety of tissues and organs, including the brain, heart, and lymphocytes, thereby asserting 11R tags as a useful delivery strategy for protein therapeutics.

In order to compare the intracellular delivery of 11R-tagged proteins with protein nanocapsules using Klf4 as a model, furin-cleavable nanocapsules with Klf4-11R were prepared and the size of nanocapsules were verified to be ~20 nm with TEM. The extent of protein delivery was directly determined by performing immunocytochemistry after culturing mouse embryonic fibroblast (MEF) cells with Klf4-11R or furin-degradable Klf4 nanocapsules. It was observed that Klf4 delivered via nanocapsule could be prominently detected in the nuclei of cells which were counterstained with Hoescht and examined using confocal microscopy. Virtually every cell nucleus showed a strong signal of Klf4 staining. The degree of staining is comparable to the positive control, BJ-iPS cells, which are neonatal human foreskin fibroblasts which have been reprogrammed into iPS cells and have high-expression levels of Klf4. In contrast, Klf4-11R showed a much weaker intensity and much less colocalization with nuclei indicating delivery of Klf4 was not as efficient. It appears that the PTD-tagged proteins often become trapped in endosomal compartments with no mechanism of release into the cytosol, and <1% of the protein cargo may be released as a result.

The prominent staining of Klf4 in the nuclei of MEF cells suggests that the nanocapsules offer more protection for preservation of protein structure and activity. In addition, the PTD-tagged proteins and other proteins which are exposed to the acidic environment in the endosome often experience degradation and loss of activity. The PTD-tagged proteins can also be degraded or subjected to proteolysis during cellular entry.

In contrast, the endoprotease-mediated delivery system of the present invention has a protective polymer layer during cellular uptake until cleavage by furin and the release of protein cargo. Collectively, these findings demonstrate that degradable nanocapsules are suitable vehicles for nuclear delivery for transcription factors. The successful nuclear delivery of Klf4 using furin-degradable nanocapsules is also particularly promising as a reprogramming tool. Direct delivery of transcription factors would allow patient-specific therapies which eliminate risks arising from genetic-based methods, including unexpected modifications in target cell genomes.

Accordingly, both cytosolic and nuclear delivery of proteins using the engineered nanocapsule carrier which degrades in response to the ubiquitous endoprotease furin, for example, was successfully demonstrated. Different cell lines were demonstrated to be amenable hosts for furin-mediated delivery, including the immortalized HeLa, the highly regenerative hAFDC, and the essential structural MEF. It was also demonstrated that protein cargos of different sizes and tertiary structures can be encapsulated and released reversibly without loss of bioactivity, including the 27 kDa 3-barrel eGFP, the 51 kDa Klf4 that has three zinc finger regions, and the 64 kDa CP3 which is a heterotetramer.

This approach will also be applicable to the intracellular delivery of other therapeutics, including small drugs, peptides, siRNA, and plasmid DNA. For example, the siRNA molecule has attracted considerable attention as a potential therapeutic agent for cancer treatment. However, an efficient and safe method for direct siRNA delivery is not available. The methods of the present invention provide an effective way to encapsulate siRNA into protease-degradable polymeric nanocapsules via the in situ polymerization, by the incorporation of positively charged monomers and specific peptide cross-linkers.

Example 7

The degradability of the polymeric shell can optionally be tuned by the sequence of the cross-linker to respond to different proteases and can be spatiotemporally controlled by using photolabile caged peptide sequences. Spatiotemporal control of the degradation process can be installed by shielding the protease recognition sequences so that light is required for cargo release. This method may be useful in the preparation and administration of protein drugs, vaccines, and other macromolecular therapeutics To demonstrate the optional spatiotemporal control of the CP3-nanocapsule degradation process, the P1 aspartic acid of the CLVDEVDTK was conjugated with a photolabile o-nitrobenzyl ester moiety ($D_m$). The resulting CL-VDEV$D_m$TK cross-linker can be cleaved by CP3 upon decaging of the aspartic acid. After brief UV exposure (λ) 365 nm, 100 W), the absorption integral area of VDEV$D_m$TK (50 μg, 1 mg/mL) at 348 nm steadily decreased, while the mass signal integral area of VDEVDTK correspondingly increased over time. Additionally, bulk free-radical polymerization using AAm and APMAAm as monomers, and CL-VDEV$D_m$TK as the cross-linker was performed. In this configuration, only upon the synergistic action of UV irradiation and CP3 hydrolysis can the polymeric matrix be dissociated from a hydrogel into a free-flowing solution.

The light-responsiveness of CP3 nanocapsules cross-linked with CL-VDEV$D_m$TK (designated CP3-$NC_{PD}$, 300 nM) was characterized by monitoring the release of pNA from Ac-DEVDpNA after different durations of UV irradiation. In the absence of UV treatment, no obvious proteolysis of the peptidyl substrate was observed. With increasing UV irradiation, the proteolytic activity of CP3-$NC_{PD}$ steadily increased and reached a maximum after 40 seconds of exposure, which is sufficiently brief to minimize UV-induced damage to cells. To demonstrate the temporal control of nanocapsule degradation, HeLa cells were first incubated with CP3-$NC_{PD}$ for 1 hour and then treated with UV for 40 seconds. After further incubation in medium for two days, nearly all cells underwent apoptosis. In contrast, cells treated with CP3-$NC_{PD}$ without UV exposure, or cells exposed to UV without CP3-$NC_{PD}$ treatment did not show significant cell death.

Similarly, cells treated with BSA-$NC_{PD}$ and irradiated with UV also maintained comparable viability to control samples, demonstrating that the combined actions of light and protease are required for degradation of the encapsulating layer.

Next, to demonstrate spatial control of nanocapsule degradation, HeLa cells were treated with 4 μM CP3-$NC_{PD}$ for one hour to facilitate internalization of the nanocapsules. After thorough washing with PBS to remove nanocapsules that were not endocytosed, a mask was applied to shield half of the culture area while exposing the other half to UV irradiation for 40 seconds. After an additional 12 hours of incubation, a prominent live/dead cell pattern that corresponds to the shielded/exposed pattern was visualized by optical microscope and assayed.

As expected, the spatial control of cell viability was only detected with the synergistic treatment of protease CP3 and UV light. Taking advantage of multiphoton caging groups (i.e., intrinsic three-dimensional resolution and reduced photodamage), this strategy could be further extended to develop a system for real protein-therapeutics, where the irradiation process needs to be performed through the target tissue.

From the discussion above it will be appreciated that the invention can be embodied in various ways, including the following:

1. An embodiment of a method for producing enzymatically-degradable nanocapsules, comprising: selecting a core cargo molecule for encapsulation; preparing a plurality of cross-linkers having at least one enzyme cleavage site; adsorbing a plurality of shell monomers to the core cargo molecule; cross-linking a plurality of adsorbed shell monomers with the cross-linkers; and polymerizing a polymeric shell around the core cargo molecule to provide a enzymatically-degradable nanocapsule; wherein the cross-linker enzyme cleavage sites of the cross-linkers are configured to be cleaved in the presence of site specific enzymes.

2. A method as recited in embodiment 1, wherein the cargo molecule is selected from the group of molecules consisting essentially of a cytokine, a transcription factor, an enzyme, a peptide, a protein, a protease and a siRNA.

3. A method as recited in embodiment 1, wherein the monomers comprise a first monomer type and a second monomer type, wherein the first monomer type and the second monomer type adsorbs with the cargo molecules and the cross-linkers cross-link both types of monomers.

4. A method as recited in embodiment 1, wherein the monomers comprise a first monomer type; and a second monomer type; wherein the first monomer type adsorbs with the cargo molecules and the second monomer type couples with the first monomer type.

5. A method as recited in embodiment 1, wherein the enzyme cleavage site of each cross-linker is a substrate for a site specific protease selected from the group of proteases consisting essentially of aspartate proteases, cysteine proteases, glutamic proteases, metalloproteases, serine proteases, threonine proteases and furin.

6. A method as recited in embodiment 1, wherein each of the cross-linkers contains more than one enzyme cleavage site.

7. A method as recited in embodiment 1, further comprising a first cross-linker construct with a first enzyme cleavage site; and a second cross-linking construct with a second enzyme cleavage site, wherein a cross-linked shell of said nanocapsule must be cleaved by more than one enzyme to release the cargo molecule.

8. A method as recited in embodiment 1, wherein the enzyme cleavage sites of the cross-linkers have an amino acid sequence that is specific for cleaving by a protease that is endogenous to a target cell.

9. A method as recited in embodiment 1, wherein a final surface charge of the polymerized nanocapsule is positive.

10. A method for selective intracellular delivery of cargo molecules to a cell or tissue, comprising selecting a target cellular system and a cargo molecule; selecting an enzyme type and cleavable peptide sequence; producing enzymatically-degradable nanocapsules, comprising selecting a core cargo molecule for encapsulation; providing a plurality of cargo molecules; preparing a plurality of cross-linkers having at least one selected enzyme cleavage site; adsorbing a plurality of shell monomers to the core cargo molecule; cross-linking a plurality of adsorbed shell monomers with the cross-linkers; and polymerizing a polymeric shell around the core cargo molecule to provide an enzymatically-degradable nanocapsule; and placing the nanocapsules in proximity to target cells or tissues to allow for penetration of target cell membranes by the nanocapsules; wherein the cross-linker enzyme cleavage sites of the cross-linkers are configured to be cleaved by site specific enzymes to release the cargo molecule.

11. A method as recited in embodiment 10, wherein the enzyme cleavage sites of the cross-linkers have an amino acid sequence that is specific for cleaving by a protease that is endogenous to a target cell.

12. A method as recited in claim 10, wherein the cargo molecule is a protease; and wherein the enzyme cleavage sites of the cross-linkers have an amino acid sequence that is specific for cleaving by the protease cargo molecule.

13. A method as recited in embodiment 10, further comprising producing a first nanocapsule with a selected cargo molecule in a nanocapsule with cross-linkers that have an amino acid sequence that is specific for cleaving by a protease that is exogenous to the target cell; producing a second nanocapsule containing a protease cargo molecule that is exogenous to the target cell with cross-linkers with an amino acid sequence that is specific for cleaving by a protease that is endogenous to a target cell; and placing said first and second nanocapsules in proximity to target cells or tissues to allow for penetration of target cell membranes by the nanocapsules; wherein the first nanocapsules are not degraded until a release of the exogenous protease cargo of the second nanocapsules.

14. A method as recited in embodiment 10, wherein the cargo molecule is selected from the group of molecules consisting essentially of a cytokine, an enzyme, a peptide, a protein, a protease and a siRNA.

15. A method as recited in embodiment 10, wherein the monomers comprise a first monomer type; and a second monomer type; wherein the first monomer type and the second monomer type adsorbs with the cargo molecules and the cross-linkers cross-link both types of monomers.

16. A method as recited in embodiment 15, wherein the first monomer comprises acrylamide and the second monomer comprises N-(3-aminopropyl) methacrylamide.

17. A method as recited in embodiment 10, wherein the monomers comprise a first monomer type; and a second monomer type; wherein the first monomer type adsorbs with the cargo molecules and the second monomer type couples with the first monomer type.

18. A method as recited in embodiment 10, wherein the enzyme cleavage site of each cross-linker is a substrate for a site specific protease selected from the group of proteases consisting essentially of aspartate proteases, cysteine proteases, glutamic proteases, metalloproteases, serine proteases, threonine proteases and furin.

19. A method as recited in embodiment 10, further comprising a first cross-linker construct with a first enzyme active site; and a second cross-linking construct with a second enzyme active site, wherein a cross-linked shell of the nanocapsule must be cleaved by more than one enzyme to release the cargo molecule.

20. A method as recited in embodiment 10, wherein a final surface charge of the polymerized nanocapsule is positive.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for producing an enzymatically degradable nanocapsule, the method comprising:

(a) selecting a core cargo for encapsulation, wherein the core cargo comprises a plurality of cargo molecules;

(b) preparing a plurality of cross-linkers having at least one enzyme cleavage site;

(c) combining a plurality of shell monomers and cross-linkers with the core cargo, wherein the plurality of shell monomers includes at least a first monomer type which physically adsorbs to said core cargo, wherein said adsorbing comprises self-assembly of the first monomer type on said core cargo via electrostatic forces between the monomers and the core cargo molecules; and (d) polymerizing a polymeric shell comprising the plurality of shell monomers and cross-linkers around the core cargo to provide a enzymatically-degradable nanocapsule;

wherein:

the cross-linker enzyme cleavage sites of the cross-linkers are configured to be cleaved in the presence of site specific enzymes.

2. The method as recited in claim 1, wherein the core cargo comprises an imaging agent, a drug, a polypeptide or a nucleic acid.

3. The method as recited in claim 1, wherein the plurality of cargo molecules comprises a plurality of different molecules.

4. The method as recited in claim 1, wherein at least two of the plurality of cargo molecules are coupled together prior to polymerizing the polymeric shell.

5. The method of claim 1, wherein cargo molecules have a surface modified with a vinyl group.

6. The method as recited in claim 1, wherein a shell monomer within the plurality of shell monomers comprises an acrylamide monomer.

7. The method as recited in claim 1, wherein the shell monomers consist essentially of:

the first monomer type; or the first monomer type and a second monomer type.

8. The method as recited in claim 1, wherein polymerizing the polymeric shell comprises an in situ free radical polymerization reaction.

9. The method of claim 1, wherein the method comprises physically adsorbing the plurality of shell monomers and the plurality of cross-linkers to said core cargo, wherein said adsorbing is modulated by electrostatic forces between the monomers and the core cargo molecule and the crosslinkers and the core cargo molecule.

10. The method of claim 9, wherein a net surface charge of the polymerized nanocapsule is positive.

11. The method of claim 1, wherein an enzyme cleavage site of the cross-linkers has an amino acid sequence that is specific for cleaving by a protease that is endogenous to a target cell.

12. The method of claim 1, wherein the enzyme cleavage site of each cross-linker is a substrate for a site specific protease selected from the group of proteases consisting of aspartate proteases, cysteine proteases, glutamic proteases, metalloproteases, serine proteases, threonine proteases and furin.

13. A method for producing an enzymatically degradable nanocapsule, the method comprising:

(a) selecting a core cargo for encapsulation, wherein:

(i) the core cargo comprises a plurality of cargo molecules;

(ii) the core cargo comprises a protein having an amino acid modified so as to allow a polymerization reaction to occur;

(b) preparing a plurality of cross-linkers having at least one enzyme cleavage site;

(c) combining a plurality of shell monomers and cross-linkers with the core cargo, wherein the plurality of shell monomers includes at least a first monomer type which physically adsorbs to said core cargo, wherein said adsorbing comprises self-assembly of the first monomer type on said core cargo via electrostatic forces between the monomers and the core cargo molecules; and (d) polymerizing a polymeric shell comprising the plurality of shell monomers and cross-linkers around the core cargo to provide a enzymatically-degradable nanocapsule;

wherein:

the cross-linker enzyme cleavage sites of the cross-linkers are configured to be cleaved in the presence of site specific enzymes.

14. The method of claim 13, wherein the amino acid is modified to comprise a vinyl group.

15. The method of claim 13, wherein the core cargo comprises the protein coupled to another cargo molecule prior to polymerizing the polymeric shell.

16. The method of claim 13, wherein the method comprises physically adsorbing the plurality of shell monomers and the plurality of cross-linkers to said core cargo, wherein said adsorbing is modulated by electrostatic forces between the monomers and the core cargo molecule and the cross-linkers and the core cargo molecule.

17. The method of claim 16, wherein a net surface charge of the polymerized nanocapsule is positive.

18. The method of claim 13, wherein an enzyme cleavage site of the cross-linkers has an amino acid sequence that is specific for cleaving by a protease that is endogenous to a target cell.

19. The method of claim 13, wherein the enzyme cleavage site of each cross-linker is a substrate for a site specific protease selected from the group of proteases consisting essentially of aspartate proteases, cysteine proteases, glutamic proteases, metalloproteases, serine proteases, threonine proteases and furin.

* * * * *